United States Patent
Jacobsen et al.

(10) Patent No.: US 8,061,205 B2
(45) Date of Patent: Nov. 22, 2011

(54) ACOUSTIC METHOD AND APPARATUS FOR DETECTION AND CHARACTERIZATION OF A MEDIUM

(75) Inventors: Jostein Jacobsen, Slalåmveien (NO);
 Åshild Bergh, S. Bera Terrasse (NO);
 Ståle Vilming, Heiasvingen (NO)

(73) Assignee: Det Norske Veritas AS, Hovik (NO)

( * ) Notice: Subject to any disclaimer, the term of this patent is extended or adjusted under 35 U.S.C. 154(b) by 404 days.

(21) Appl. No.: 12/298,514

(22) PCT Filed: Apr. 25, 2007

(86) PCT No.: PCT/NO2007/000142
§ 371 (c)(1),
(2), (4) Date: Apr. 17, 2009

(87) PCT Pub. No.: WO2007/123418
PCT Pub. Date: Nov. 1, 2007

(65) Prior Publication Data
US 2009/0308161 A1 Dec. 17, 2009

(30) Foreign Application Priority Data
Apr. 26, 2006 (NO) .................................. 20061835

(51) Int. Cl.
*G01N 29/12* (2006.01)

(52) U.S. Cl. ................. 73/579; 73/592; 73/629; 73/659
(58) Field of Classification Search .................... 73/579, 73/53.06, 54.25, 589, 592, 602, 599, 629
See application file for complete search history.

(56) References Cited

U.S. PATENT DOCUMENTS

| | | | |
|---|---|---|---|
| 6,513,385 B1 * | 2/2003 | Han et al. ....................... 73/629 |
| 6,644,119 B1 * | 11/2003 | Sinha .............................. 73/579 |
| 7,114,390 B2 * | 10/2006 | Lizon et al. ................. 73/290 V |
| 7,523,640 B2 * | 4/2009 | DiFoggio et al. ............ 73/19.03 |
| 7,921,691 B2 * | 4/2011 | DiFoggio et al. ............ 73/19.03 |
| 7,963,165 B2 * | 6/2011 | Sinha .............................. 73/623 |

* cited by examiner

*Primary Examiner* — J M Saint Surin
(74) *Attorney, Agent, or Firm* — Abelman, Frayne & Schwab

(57) ABSTRACT

An acoustic method and apparatus detects or characterizes a medium in a structure which may be a container, such as a pipeline for transportation of oil, gas, or hydrocarbon condensate. A pulse of broadband acoustic energy is emitted towards the structure by a first transducer. A return signal is generating by a second transducer from acoustic energy returned from the structure in response to the emission of acoustic energy. A return signal spectrum representing acoustic spectral components of the acoustic energy returned from the structure is derived from the return signal, and the medium is detected or characterized by applying a return signal processing medium detection or characterization algorithm to the return signal spectrum.

14 Claims, 7 Drawing Sheets

ACOUSTIC METHOD AND APPARATUS FOR DETECTION AND CHARACTERIZATION OF A MEDIUM

CROSS-REFERENCE TO RELATED APPLICATIONS

This application is a 371 of international application number PCT/NO2007/000142, filed on Apr. 25, 2007.

BACKGROUND OF THE INVENTION

1. Field of the Invention

The present invention relates to detecting the presence of a hydrate deposit or a condensate in a container, more specifically in a pipeline, by identifying certain characteristics of an acoustic signal emitted from a wall of the container in response to a spectrally broad acoustic signal being transmitted from a transducer, towards the container.

2. Description of the Related Art

Acoustic Resonance Technology (ART) is a technology where the ability of applying acoustic energy to create resonances is utilized. If a plate or pipe is insonated by an acoustic energy pulse, and the acoustic energy comprises wave components with frequencies having wavelengths corresponding to twice or integral numbers of the thickness of the plate or pipe wall, these frequencies will create standing waves across the plate or pipe wall. When the pulse comes to an end, reradiated resonant energy is detected, typically by way of a hydrophone located at a distance from the plate.

It is to be understood that, in the context of the description provided herein of the present invention, the term container is applicable to any arrangement being capable of confining a medium with respect to its surroundings, such as for example a pipeline designed for transporting oil, gas or other media that may be transported by a pipe arrangement.

The frequencies applied in the acoustic energy pulse will typically be a decade or more lower than the frequencies applied in traditional ultrasound techniques, thus offering ability to penetrate layered materials and provide characterization of various media. The energy content in the "resonant part" of the energy being returned upon insonation, and total reflected energy, is influenced by the medium on both sides of the plate or pipe wall. The medium outside submerged gas pipelines is typically seawater, while the medium contained inside the pipeline may be gas, condensate, or, occasionally, hydrate. Acoustic characteristics of these internal media will result in variations in acoustic energy being returned from the pipe when insonated by acoustic energy.

BRIEF SUMMARY OF THE INVENTION

The present inventors have found that the respective acoustic impedances of gas, hydrate and condensate are different from each other, and that returned resonance energy exhibiting different properties for at least these three cases, i.e. gas, hydrate and condensate, can be employed for determining the type of medium being present at a particular location within a container such as pipe.

The invention provides a solution for detecting the presence of a hydrate deposit or a condensate in a container, more specifically in a pipeline, by identifying certain characteristics of an acoustic signal emitted from a wall of the container in response to a spectrally broad acoustic signal being transmitted from a transducer, towards the container.

The solution of the invention provides the method for detection or characterization of a medium comprised in a structure, the method comprising the steps of: emitting by a first transducer means a pulse of broadband acoustic energy towards the structure, generating by a second transducer means a return signal from acoustic energy returned from the structure in response to the emitting, deriving from the return signal a return signal spectrum representing acoustic spectral components of the acoustic energy returned from the structure, and detecting or characterizing the medium by applying a return signal processing medium detection or characterization algorithm to the return signal spectrum.

The solution of the invention provides the apparatus for detection or characterization of a medium comprised in a structure, the apparatus comprising: a first transducer means for emitting a pulse of broadband acoustic energy towards the structure, a second transducer means for generating a return signal from acoustic energy returned from the structure in response to the emitting, a spectrum deriving means for deriving from the return signal a return signal spectrum representing acoustic spectral components of the acoustic energy returned from the structure, and a medium detection or characterization means for detecting or characterizing the medium, the medium detection or characterization means adapted to detect or characterize the medium by applying a return signal processing medium detection or characterization algorithm to the return signal spectrum.

DETAILED DESCRIPTION OF THE INVENTION

The present invention is related to international application number PCT/NO2007/000142, filed on Apr. 25, 2007, which is incorporated herein by reference in its entirety.

As used herein, a reflection spectrum is a spectrum which is a result of computing a Fast Fourier Transform (FFT) of the part of a time series starting a number n, well in advance of the first energy of the first reflected pulse reaching the receiver.

Figure 4:
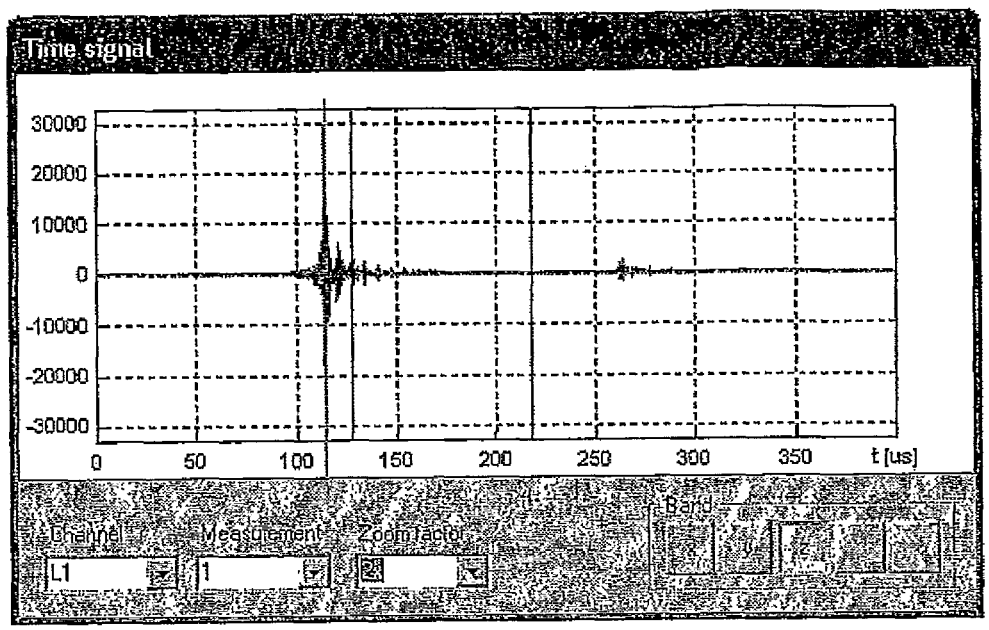
FIG. 4 is an example of a time series of the reflected signal from the low frequency transducer element, z.

This number n depends on the pulse, and on the analog-to-digital (AD) converter applied used. An example is shown in FIG. 4, where the solid, vertical lines indicate the limits of the FFT.

Figure 5:
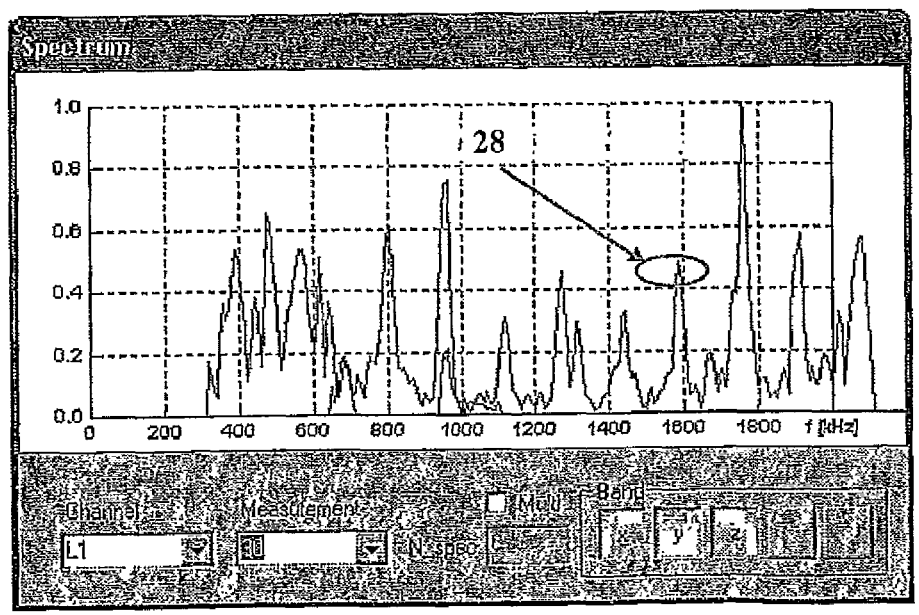
FIG. 5 is an example of a tail spectrum of all transducer elements put together.
Figure 6:
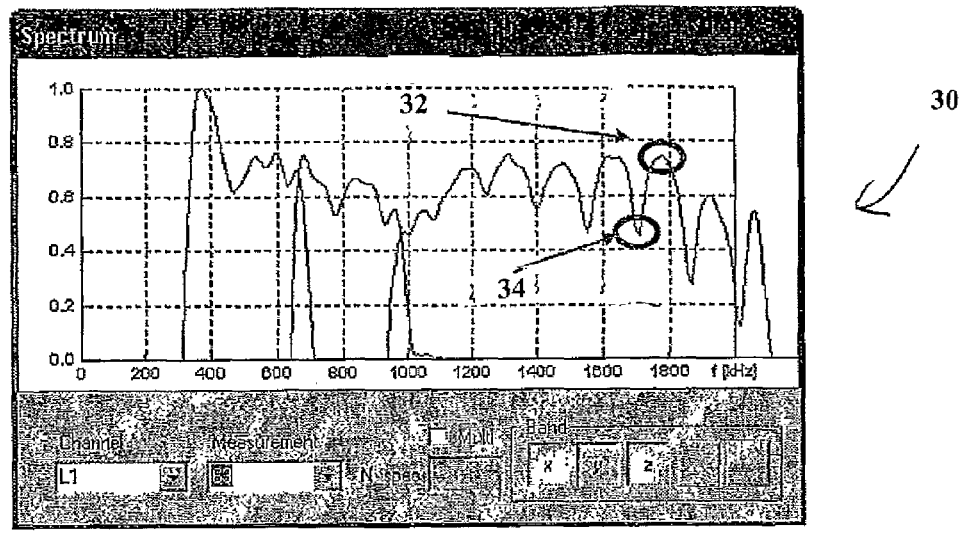
FIG. 6 is an example of a reflection spectrum of all transducer elements put together.

As used herein, a tail spectrum is a spectrum which is a result of computing a FFT of the part of a time series containing the resonant energy emitted from the pipe wall. The FFT starts subsequent to the first reflected pulse, counting a number n from the maximum of the first reflection. This number n depends on the pulse, and on the AD converter applied. Examples are shown in FIGS. 5 and 6, where the FFT limits are shown as solid, vertical lines.

Both spectra are most convenient produced from the first total reflection reaching the receiver transducer, but may as well be the result of applying the FFT algorithm on the second, third and following reflections as long as the signal to noise ratio is acceptable.

Referring to FIGS. 1-11, the present invention detects the presence of a hydrate deposit or a condensate in a container, more specifically in a pipeline, by identifying certain characteristics of an acoustic signal emitted from a wall of the container in response to a spectrally broad acoustic signal being transmitted from a transducer, towards the container.

In an example apparatus 10, an acoustic transducer 12 applies acoustic signals through water 14 and through a steel or metal wall 16 of a pipeline into a material 18 such as a condensate, a gas, or a hydrate.

Figure 2:
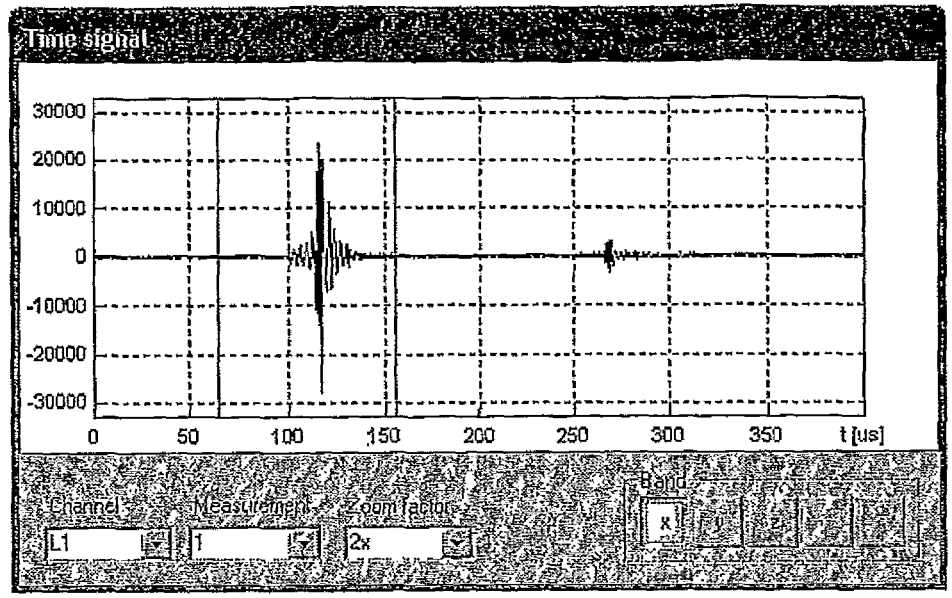
FIG. 2 is an example of a time series of the reflected signal from the low frequency transducer element, x.
Figure 3:
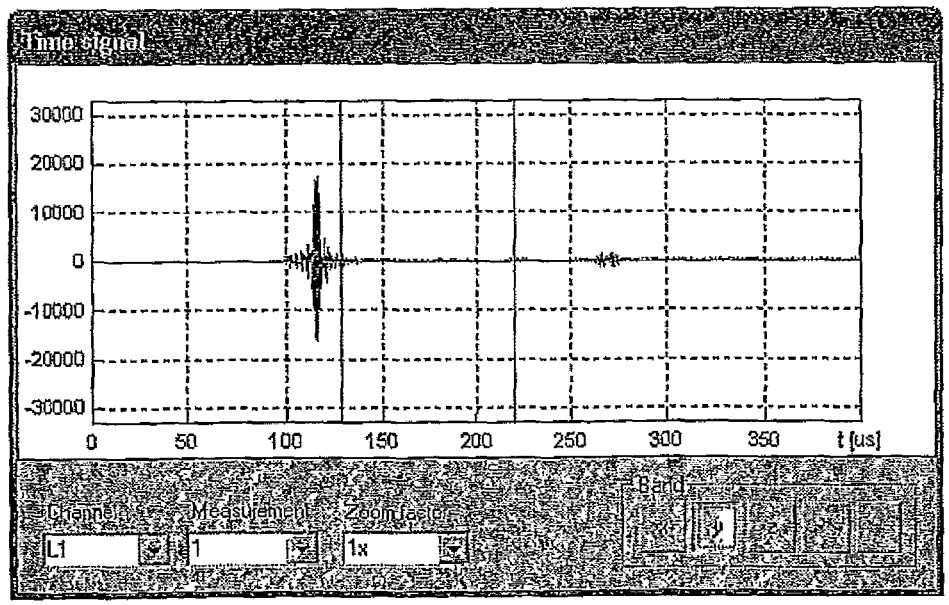
FIG. 3 is an example of a time series of the reflected signal from the low frequency transducer element, y.

FIG. 2 is an example of a time series of the reflected signal from the low frequency transducer element, x, shown on a display 20, indicating where a FFT of a first reflection part is computed. FIG. 3 is an example of a time series of the reflected signal from the low frequency transducer element, y, shown on a display 22, indicating where a FFT of a tail is computed. FIG. 4 is an example of a time series of the reflected signal from the low frequency transducer element, z, shown on a display 24, indicating where a FFT of a tail is computed.

FIG. 5 is an example of a tail spectrum of all transducer elements put together, shown on a display 26, with an nth harmonic 28. FIG. 6 is an example of a reflection spectrum of all transducer elements put together, shown on a display 30, with an nth maximum 32 and an nth minimum 34.

Figure 7:
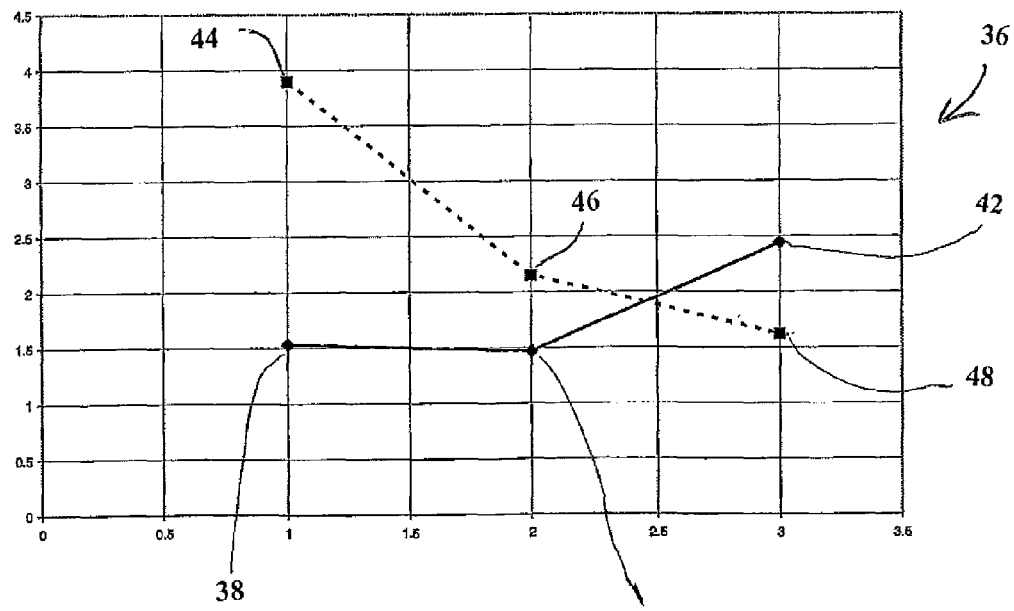
FIG. 7 is a graph representing an example of an application of an algorithm of the invention applied to a sample spectrum.

FIG. 7 is a graph 36 representing an example of an application of an algorithm of the invention applied to a sample spectrum for algorithm A1 for Examples 1 and 2, described herein, and for algorithm A2 for Example 3, described herein, applied on a dataset from a pipe section with gas inside, indicated by diamonds at data points 38-42, and applied on a dataset from a pipe section with condensate inside, indicated by squares at data points 44-48.

Figure 8:
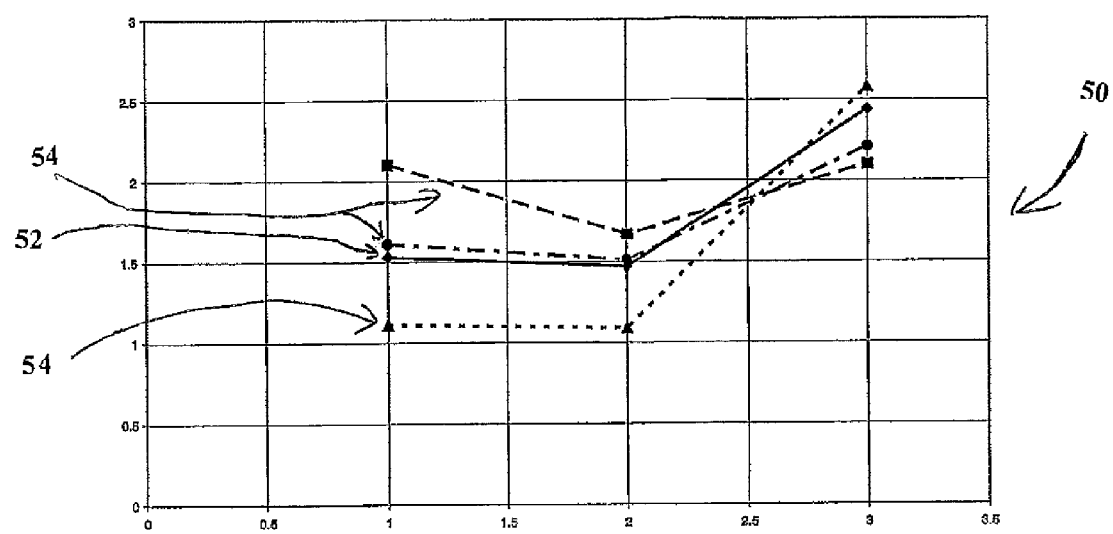
FIG. 8 is a graph representing an example of an application of a further algorithm of the invention applied to a sample spectrum.

FIG. 8 is a graph 50 representing an example of an application of a further algorithm of the invention applied to a sample spectrum for algorithm A1 for Examples 1 and 2, described herein, and for algorithm A2 for Example 3, described herein, applied on a dataset from a pipe section with gas inside, indicated by diamonds at data points 52, and applied on a dataset from a pipe section with condensate inside, indicated by squares, circles, and triangles at data points 54.

Figure 9:
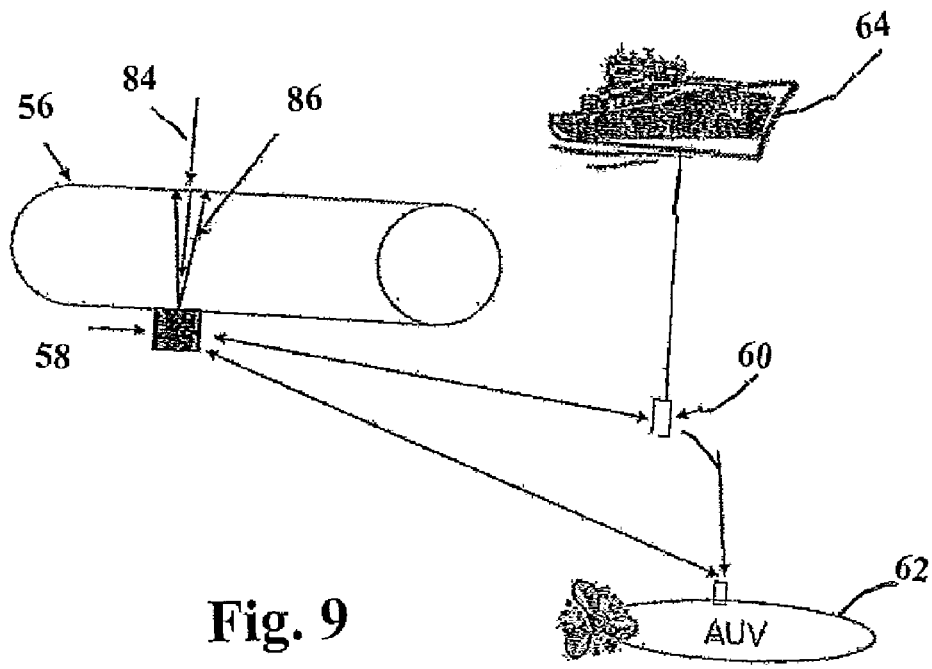
FIG. 9 shows an example with the Hydrate Detection Unit as a fixed installation.

FIG. 9 shows an example with the Hydrate Detection Unit used in Example 1, described herein, as a fixed installation with a pipeline 56 having a fixed transducer and electronics 58, an Extreme Low Frequency (ELF) unit 60, an Autonomous Underwater Vehicle (AUV) 62, a survey vessel 64, with reflected signals 84 and emitted acoustic signals 86 being generated and detected. Power and low frequency communications may be provided by a seawater battery or by indicative powering from a Remote Operated Vehicle (ROV) or by the AUV 62.

Figure 10B:
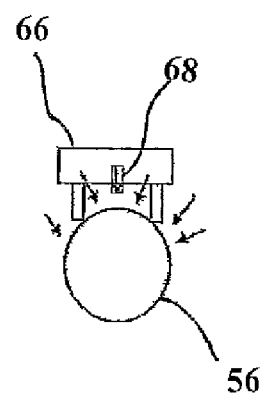
FIGS. 10*a* and 10*b* show a side perspective view and a front elevational view, respectively, of an example of the Hydrate Detection Unit mounted on a Remote Operated Vehicle (ROV)
Figure 10A:
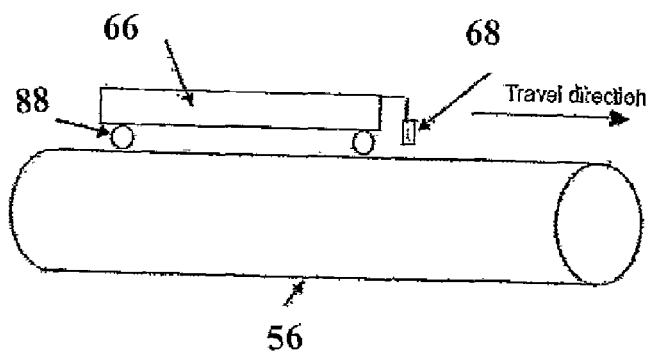

FIGS. 10a and 10b show a side perspective view and a front elevational view, respectively, of an example of the Hydrate Detection Unit used in Example 2, described herein, mounted on a ROV 66, with an acoustic sensor array 68 for moving in the travel direction along the length of the pipeline 56 using wheels or bells 88.

Figure 11:
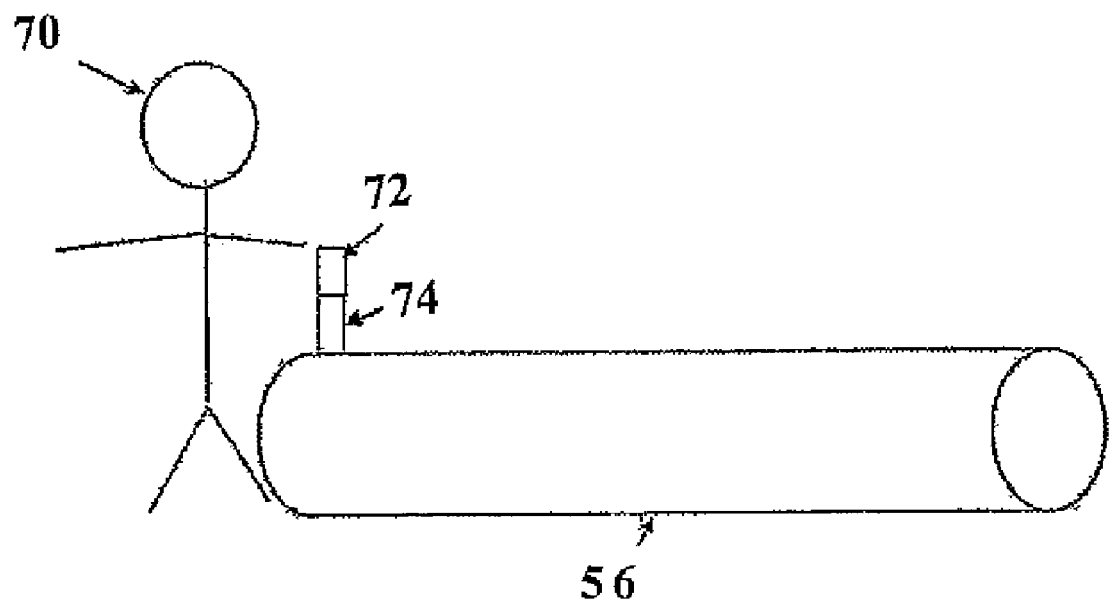
FIG. 11 shows an example of the Hydrate Detection Unit mounted in a handheld unit.

FIG. 11 shows an example of the Hydrate Detection Unit used in Example 3, described herein, mounted in a handheld unit used by an inspector 70, who passes the unit over the pipeline 56. The handheld unit includes a transducer and electronics 72, and a waveguide 74 attached to the transducer and electronics 72.

Displayed on a timeline, the return signal includes energy representing of a number of reflections emanating from the front wall of the container, in addition to further acoustic energy emanating from other boundaries between materials having different acoustic impedances on respective sides of the boundaries. Also included is the possible resonant energy built up inside the pipe wall during insonification, and later reradiated from the boundaries.

The acoustic signal returned from the container is a time signal that varies over time, examples are shown in FIGS. 4-6, and which is processed by applying an FFT algorithm to parts of the first reflection emitted from the front wall for the purpose of converting this part of the time signal to a frequency spectrum.

Further spectra derived are called reflection spectrum or a tail spectrum, depending on the portion of the time varying signal to which the FFT is applied.

To determine the presence of gas, condensate or hydrate inside the pipe, one or more algorithms are applied the spectrum, or spectra, that has been obtained as suggested above. The algorithms are designed to calculate and extract specific parameters and corresponding values from the reflection spectrum or tail spectrum, and the resulting values of these parameters are used for determining the type of medium located inside the pipe at the particular position at which the measurement is made. The algorithms may be applied to a single measurement, or to the resulting reflection, and tail spectrum achieved by applying a comparison and filtering technique involving a number of measurements as input.

The present invention provides a method for detection of gas hydrates in pipelines over a selected area of a container, characterized in that it includes:

1) generating broadband electrical excitation signals which include frequency components within the test area in question;

2) converting aforementioned broadband electrical excitation signals into broadband acoustic signals;

3) transmitting the aforementioned broadband acoustic signals into the object to be measured;

4) receiving acoustic response signals emitted from the object to be measured in response to the aforementioned transmitted broadband acoustic signals;

5) converting the aforementioned acoustic response signals emitted by the object into electrical receiver signals;

6) conditioning the aforementioned receiver signals;

7) analyzing conditioned receiver signals to derive spectral distribution of the signal energy in the aforementioned conditioned receiver signals; and 8) applying algorithms which classify the medium inside the pipe as gas, condensate or hydrate, based on the values delivered by the applied algorithms.

For storage of the measuring results for subsequent processing or, for example, for planning and carrying out later similar investigations, the method also includes storage of the different results of the classification process. That means storage of both the time series registered by the receiver transducer, the calculated reflection and tail spectrum, the computed values of the applied algorithms, and the classification as gas, condensate or hydrate which is the final results linked to each measurement.

Furthermore, it may be advantageous for an operator or inspector to be given an immediate presentation of the results in order to, for example, either monitor the quality of the results or to decide immediately any measures required in consequence of the results obtained. The method could, therefore, also include a step for the presentation of the results with associated processing for presentation in a manner suitable for presenting the results.

The generation of broadband excitation signals is typically be done with the aid of an electronic signal generator which can be set for an suitable signal form and signal strength, preferably by means of a control unit which monitors the returned signal. A suitable excitation signal can be characterized as follows: the excitation signal is split up into a number of separate excitation pulses: each individual excitation pulse may have any form that has a frequency content which covers the entire frequency range in question; examples of pulse forms include $\sin(x)/x$, chirp, transient and white noise; the duration of each individual excitation pulse is adjusted so that it does not interfere with the reflected signal or response from the object subjected to measurement; the time interval between each excitation pulse has been adapted so that reflected pulse from the structure has fallen below a given level; the power content in each individual pulse is adjusted, preferably automatically, within given limits until the power in the reflected signal has reached a desired level; and the characteristic parameters for the pulse are controlled by software in the control unit.

Upon insonation of the object, such as a pipe, by a broadband acoustic pulse signal, a typical return signal that is received and processed by the method according to the invention can be characterized as follows: the signal consists of two main parts, a "primary reflection" and a "tail"; any of the "primary reflection" portion and the "tail" portion can be used for characterization of the medium inside the pipe; the software running in a computer which makes the analysis and computation determines, on the basis of given criteria, which parts of the reflected signal and "tail" are to be given importance in the characterization of the media inside the pipe to be analyzed; and the power level of the part of the return signal which it is desirable to use for the characterization is adapted to the measuring range of the AD converters by controlling emitted power and/or adjusting the amplification of the received, return signal; whereby the method advantageously carries out adjustment of the amplitude of the received return signal by automatic control through the software by autoranging.

The signal processing and the medium characterization made by means of the method according to the invention may include the following: a FFT is taken of the portion of the return signal that it is desirable to use in the medium characterization; based on the FFT, an energy spectrum is formed which describes the energy content in the return signal as a function of frequency; one or more of the developed algorithms are applied to one or more of the energy spectra computed; the medium inside the pipe at the particular site is then characterized as gas, hydrate or condensate; and the phase in the response signal is optionally analyzed in conjunction with energy considerations, or alone, to further enhance the measurements.

The invention also provides an apparatus for carrying out detection or characterization of a medium located in a part of a container object to be measured over a selected part of the container, characterized in that it comprises: 1) a signal generator for generating a broadband, electrical excitation signal; 2) a broadband sensor having at least one transducer for converting the electrical excitation signal into an acoustic excitation signal, transmitting the acoustic excitation signal, receiving an acoustic response signal and converting the acoustic response signal into an electrical receive signal; 3) a processing means for conditioning and spectral analysis of the receive signal; 4) a calculating means for applying at least one detection or characterization algorithm to an output from the processing means and thereby characterizing the medium as gas, hydrate or condensate; and 5) a control means operatively connected to, the signal source, sensor, processing means and calculating means, for the control thereof of the apparatus.

For storing the results from the measurements, the apparatus will also include one or more registration means connected to the control means and calculating means. A number of different devices may conceivably be used for storage of the results, such as disc storage, machine readable paper print-outs, punch tapes and the like.

To allow observation of results at various stages of signal processing, application of algorithms, etc., by, for example, an operator or an inspector, the apparatus will also include one or more data output means connected to the control means and the calculating means for processing and presentation of the computed medium characteristics. The output devices which are suitable for this purpose may, for example, be paper-based printers, display screens having either color or monochrome reproduction of the cathode-ray type, the plasma type, the liquid crystal display (LCD) type or the like.

Transducers and configurations of such which are suitable for the purposes of providing an excitation signal or for receiving an acoustic return signal may also be described by the following: a transducer element can be adapted to either only transmit or only receive, or to both transmit and receive; if desirable, the choice may be made, in a multi transducer sensor, to transmit on selected elements and receive on other elements; the excitation pulse can be transmitted to all the elements of a multi transducer sensor simultaneously or only to selected transducer elements; and the configuration of excitation transducers can be controlled by means of the software in the control means.

Thus, a first transducer means for emitting an excitation signal and a second transducer means for receiving an return signal may be embodied by a single transducer means.

In the following, the algorithms of the invention are explained in more detail.

ALGORITHM 1

Algorithm 1 will now be explained with reference to FIG. 6. This algorithm operates on a reflection spectrum as shown in FIG. 6 and calculates the ratio $$A1 = \text{Max}_n / \text{Min}_n$$

of the n'th maximum and the corresponding n'th minimum just to the left of the n'th maximum of this reflection spectrum. Then it checks the resulting value against preset ranges which characterize different media.

ALGORITHM 2

Algorithm 2 will now be explained with reference to FIG. 6. This algorithm operates on a reflection spectrum as shown in FIG. 6, and calculates the ratio $$A2 = Max_n / Min_{n-k}$$

of the n'th maximum and the (n'th-k'th) maximum of the reflection spectrum, where k is a number ranging from 1 to n. This ratio is a sort of a gradient of a part of the spectrum. The ratio is checked against preset ranges of numbers which characterize the different media which could be inside the particular pipe.

ALGORITHM 3

Algorithm 3 will now be explained with reference to FIG. 5. This algorithm operates on a 'tail' spectrum as shown in FIG. 5, and calculates the difference $$A3 = f_{n,Theoretical} - f_{n,Measured}$$

between a preset value of the n'th harmonic based on the knowledge of the pipe thickness, and the actual value extracted from a tail spectrum, and compare the difference with a preset range of frequency shifts characterizing the different media which could be inside the particular pipe.

ALGORITHM 4

Algorithm 4 will now be explained with reference to FIG. 5. This algorithm operates on a tail spectrum as shown in FIG. 5, and calculates a sum of the energy levels $$A4 = \Sigma EnergyLevel(f_n)$$

of n of the harmonics of the tail spectrum, where n=0, 1, ... MaxHarmonic, and compares the resulting value with a preset range of values characterizing the different possible media inside the particular pipe.

ALGORITHM 5

Algorithm 5 will now be explained with reference to FIGS. 5 and 6. This algorithm operates on a reflection spectrum or on a tail spectrum, as shown in FIG. 5 and FIG. 6, and calculates the standard deviation $$A5 = STDEV(AN_m)$$

of the results of applying algorithm 1, 2, 3 or 4 on a number of successive reflection spectra or tail spectra, where N=1, 2, 3 or 4, and m is the number of results used for computing the standard deviation, and compares the result with a preset range of values characterizing different media.

ALGORITHM 6

Algorithm 6 will now be explained with reference to FIGS. 5 and 6. This algorithm operates on a reflection spectrum, a tail spectrum or both, as shown in FIG. 5 and FIG. 6, and combines the results of two or more of the above listed algorithms. An example would be:

$$A6 = A1 + A2.$$

EXAMPLES

Figure 1:
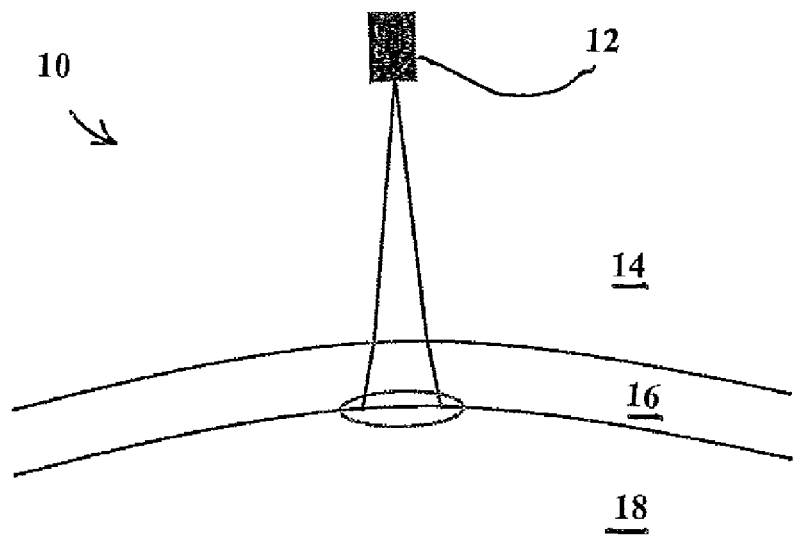
FIG. 1 is a sketch of the measuring situation, with a transducer emitting acoustic energy against a part of a gas pipe wall. The energy reflected from the inner part of the pipe wall will be different if hydrate is inside compared to the situation when gas is inside the pipe.

The following examples are explained with reference to FIG. 1, FIG. 6, FIG. 8 and FIG. 9. A broadband acoustic transducer has been applied to the measurements on different pipe sections containing gas, condensate and hydrate, as shown in FIG. 1. After conditioning the signals to obtain reflection spectra as shown in FIG. 6, algorithm A1 has been applied with n=10 in Example 1 and n=11 in Example 2, and algorithm A2 has been applied with n=11, and k=5 in Example 3. The results are shown in FIG. 8 and FIG. 9.

Gas Hydrate Detection

Example 1

Example 1 will now be explained with reference to FIG. 9. A combined transducer and electronics module, preferably also including signal processing, is be mounted on a gas pipeline at predefined locations, as defined by the oil company in question. Fixed mounting will provide the oil company with valuable information with respect to being able to detect hydrate build up at an early stage, thus enabling corrective measures, like e.g. methanol injection, in order to prevent a hydrate plug to develop to the point where it blocks the gas flow.

The transducer module may be powered by e.g. a seawater battery, although a more preferred solution is inductive powering from a communication module lowered by a survey vessel or from an Autonomous Underwater Vehicle (AUV), or from a (ROV). Preferred communication between survey vessel, AUV or ROV and the fixed transducer module may typically be wireless communication through use of Extreme Low Frequency (ELF) communication methods.

Gas Hydrate Detection

Example 2

Example 2 will now be explained with reference to FIG. 10. A preferred method for scanning through continuous and variable repetition rates, and identification of possible hydrate plugs is through use of a ROV which crawls on top of the pipeline. The ROV will have mounted a sensor comprising a transducer array of one or more transducers, arranged such that a predefined portion of a circumference of the pipeline is covered. The data will be sent through the ROV umbilical for signal processing topside. The stand-off distance between the transducer and the pipeline is not critical and may advantageously be between 50 mm and 300 mm.

Gas Hydrate Detection

Example 3

Example 3 will now be explained with reference to FIG. 11. The transducer and electronics module may be combined with a waveguide means for transfer of acoustic signals, and used in air by a surveyor on pipes exposed to hydrates in e.g. oil refineries. The unit need to be in contact with the pipe. A preferred waveguide design may be as outlined in Norwegian patent NO 314554. Signal processing is carried out by a processing means comprised in the handheld, and results may be displayed, on site, and in real time.

What is claimed is:

1. An acoustic method for detection or characterization of a medium contained in a structure, the structure having a first wall being located adjacent to the medium, the method comprising:

emitting by a first transducer means a pulse of broad banded acoustic energy towards the first side of the first wall of the structure, the broad banded acoustic energy including at least one frequency corresponding to an acoustic resonance frequency of the first wall, generating by a second transducer means a return signal from acoustic energy returned from the first wall of the structure in response to the emitting, deriving from the return signal a return signal spectrum representing acoustic spectral components of the acoustic energy returned from the first wall of the structure, and detecting or characterizing the medium by applying a return signal processing medium detection or characterization algorithm to the return signal spectrum.

2. An acoustic apparatus for detection or characterization of a medium contained in a structure, the structure having a first wall being located adjacent to the medium, the apparatus comprising:

a first transducer means for emitting a pulse of broad banded acoustic energy towards the first side of the first wall of the structure, the broad banded acoustic energy including at least one frequency corresponding to an acoustic resonance frequency of the first wall, a second transducer means for generating a return signal from acoustic energy returned from the first wall of the structure in response to the emitting, a spectrum deriving means for deriving from the return signal a return signal spectrum representing acoustic spectral components of the acoustic energy returned from the first wall of the structure, and a medium detection or characterization means for detecting or characterizing the medium, the medium detection or characterization means adapted to detect or characterize the medium by applying a return signal processing medium detection or characterization algorithm to the return signal spectrum.

3. An acoustic method for detection of a hydrate presence in an internal cavity of a pipeline for hydrocarbon transport, the pipeline comprising a forward wall, a rear wall and the internal cavity located between the forward wall and the rear wall, the method comprising:

emitting from a transmitting point a first acoustic pulse wave train towards the forward wall of the pipeline, the first wave train comprising a plurality of acoustic waves of different frequencies including at least one frequency corresponding to an acoustic resonance frequency of the forward wall or of the internal cavity;

receiving at or close to the transmitting point a second wave train returned from the forward wall as a result of a resonance in the forward wall, the second wave train having at least one of the plurality of acoustic waves;

determining the volume of waves in the second wave train having frequencies different from frequencies of the first wave train; and determining the hydrate presence in the internal cavity of the pipeline at least on the basis of the determined volume of waves in the second wave train having the different frequencies.

4. An acoustic method according to claim 3, the method comprising:

receiving at or close to the transmitting point a third wave train returned from the forward wall as a result of reflection from the forward wall;

determining the volume of waves in the third wave train having frequencies different from frequencies of the first wave train; and determining further the hydrate presence in the internal cavity of the pipeline on the basis of the determined volume of waves in the third wave train having the different frequencies.

5. An acoustic method according to claim 3, the method comprising:

receiving at or close to the transmitting point a fourth wave train returned from the rear wall as a result of resonance in the rear wall having at least one of the plurality of acoustic waves;

determining the volume of waves in the fourth wave train having frequencies different from frequencies of the first wave train; and determining further the hydrate presence in the internal cavity of the pipeline on the basis of the determined volume of waves in the fourth wave train having the different frequencies.

6. An acoustic method according to claim 3, the method comprising:

receiving at or near the transmitting point a fifth wave train returned from the rear wall as a result of reflection from the rear wall;

determining the volume of waves in the fifth wave train having frequencies different from frequencies of the first wave train; and, determining further the hydrate presence in the internal cavity of the pipeline on the basis of the determined volume of waves in the fifth wave train having the different frequencies.

7. An acoustic method for detection of a hydrate presence in an internal cavity of a pipeline for hydrocarbon transport, the pipeline comprising a forward wall, a rear wall and the internal cavity located between the forward wall and the rear wall, the method comprising:

emitting from a transmitting point a first acoustic pulse wave train towards the forward wall of the pipeline, the first acoustic pulse wave train comprising a plurality of acoustic waves of different frequencies in a frequency range of a dominant acoustic resonance for the forward wall or the rear wall;

receiving at or close to the transmitting point a second wave train returned from the forward wall as a result of the dominant acoustic resonance in the forward wall or the rear wall having at least one acoustic wave from among the plurality of acoustic waves;

determining the volume of waves in the second wave train having frequencies in the dominant resonance frequency range; and determining the hydrate presence in the internal cavity of the pipeline on the basis of a frequency displacement of dominant resonance frequency waves in the second wave train.

8. An acoustic apparatus for detection of hydrate presence in a pipeline for hydrocarbon transport, wherein the apparatus is designed to perform the method according to claim 3.

9. The method of claim 1, wherein the acoustic energy returned is a reflection from the first wall, and the return signal processing medium detection or characterization algorithm comprises:

calculating the ratio $A1 = Max_n/Min_n$ of the nth maximum and the corresponding minimum just to the left of the nth maximum of the reflection spectrum, and checking the resulting value against preset ranges which characterize different media.

10. The method of claim 1, wherein the acoustic energy returned is a reflection from the first wall, and the return signal processing medium detection or characterization algorithm comprises:

calculating the ratio $A2 = Max_n/Max_{n-k}$ of the nth maximum and the (nth−kth) maximum of the total reflection spectrum, where k is a number ranging from 1 to n, the ratio representing a gradient of a part of the spectrum, and checking the ratio against preset ranges of numbers which characterize different media which are contained in the structure.

11. The method of claim 1, wherein the acoustic energy returned is resonant reverberation from the first wall, and the return signal processing medium detection or characterization algorithm comprises:

calculating the difference between a preset value of the nth harmonic based on the knowledge of the pipe thickness and the actual value extracted from a tail spectrum $A3 = f_{n,Theoretical} - f_{n,Measured}$, and comparing the difference with a preset range of frequency shifts characterizing the different media which are contained in the structure.

12. The method of claim 1, wherein the acoustic energy returned is resonant reverberation from the first wall, and the return signal processing medium detection or characterization algorithm comprises:

calculating the energy level of n of the harmonics of the tail spectrum $A4 = \Sigma\, EnergyLevel(f_n)$ where n=0, 1, ... Max-Harmonic, and comparing the resulting value with a preset range of values characterizing the different possible media which are contained in the structure.

13. The method of claim 9, further comprising:

calculating the standard deviation of the resulting obtained on a number of successive reflection spectra or reverberation spectra $A5 = STDEV(AN_m)$ where N=1,2,3 or 4, and m is the number of results used for computing the standard deviation, and comparing the calculated standard deviation with a preset range of standard deviation values characterizing different media which are contained in the structure.

14. The method of claim 9, further comprising:

calculating the sum of the resulting values $A6 = A1 + A2$, and comparing the calculated sum with a preset range of standard deviation values characterizing different media which are contained in the structure.

\* \* \* \* \*

UNITED STATES PATENT AND TRADEMARK OFFICE
CERTIFICATE OF CORRECTION

| | |
|---|---|
| PATENT NO. | : 8,061,205 B2 |
| APPLICATION NO. | : 12/298514 |
| DATED | : November 22, 2011 |
| INVENTOR(S) | : Jostein Jacobsen, Ashild Bergh and Stale Vilming |

Page 1 of 1

It is certified that error appears in the above-identified patent and that said Letters Patent is hereby corrected as shown below:

On the Title page, add:

Related U.S. Application Data

(60) Provisional application No. 60/794,859, filed on April 26, 2006

Signed and Sealed this
Fourteenth Day of February, 2012

David J. Kappos
*Director of the United States Patent and Trademark Office*